United States Patent

Nomura et al.

[11] Patent Number: 5,693,651
[45] Date of Patent: Dec. 2, 1997

[54] QUINOLINE DERIVATIVES

[75] Inventors: Yutaka Nomura, Chiba; Shogo Sakuma; Seiichiro Masui, both of Saitama, all of Japan

[73] Assignee: Nippon Chemiphar Co., Ltd., Tokyo, Japan

[21] Appl. No.: 809,592
[22] PCT Filed: Oct. 20, 1995
[86] PCT No.: PCT/JP95/02167
  § 371 Date: Mar. 26, 1997
  § 102(e) Date: Mar. 26, 1997
[87] PCT Pub. No.: WO96/12719
  PCT Pub. Date: May 2, 1996

[30] Foreign Application Priority Data

Oct. 20, 1994 [JP] Japan ................................. 6-281301
Aug. 3, 1995 [JP] Japan ................................. 7-218056

[51] Int. Cl.[6] ................ C07D 413/06; C07D 417/06; A61K 31/47
[52] U.S. Cl. ................ 514/314; 514/256; 514/269; 544/333; 546/172; 546/175
[58] Field of Search ................ 544/333; 546/172, 546/175; 514/256, 269, 314

[56] References Cited

FOREIGN PATENT DOCUMENTS 0267580 11/1986 Japan.

OTHER PUBLICATIONS

Chemical Abstracts, vol. 71, No. 13, Abstract No. 61, 742f, Sep. 29, 1969, p. 512.

*Primary Examiner*—Zinna Northington Davis
*Attorney, Agent, or Firm*—McAulay Fisher Nissen Goldberg & Kiel, LLP

[57] ABSTRACT

The invention has an object to provide a novel quinoline derivative of the following formula (I) which has no benzyl group in the 5-position and shows hypoglycemic effect, particularly, by oral administration:

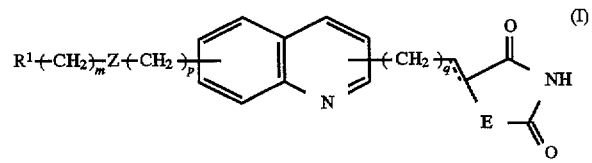

in which $R^1$ is hydrogen; an alkyl group of 1–6 carbon atoms, an amino group of the formula of —$NR^4R^5$ in which each of $R^4$ and $R^5$ independently is hydrogen, alkyl of 1–6 carbon atoms, phenyl, pyridyl, pyrimidyl or benzoyl; or a phenyl group, a naphthyl group, a cycloalkyl group having 3 to 8 carbon atoms, or a 5 to 8 membered heterocyclic group comprising, as ring-constituting atoms, 1 to 2 nitrogens, oxygens or sulfurs and remaining carbon atoms, each of which may have, as a substituent, alkyl of 1–6 carbon atoms, alkoxy of 1–6 carbon atoms, halogen, hydroxyl, halogenoalkyl of 1–6 carbon atoms, halogenoalkoxy of 1–6 carbon atoms, nitro, amino, phenyl, thienyl, furyl, thiazolyl or pyridyl; Z is O, S, C=O, or $CH_2$; E is S or O; m is an integer of 0 to 4; p is an integer of 0 to 4; q is an integer of 0 to 4; and the double line composed of a broken line and a solid line means a single or double bond.

3 Claims, No Drawings

QUINOLINE DERIVATIVES

This application is a 371 of PCT/JP95/02167 filed Oct. 20, 1995.

Field of the Invention

This invention relates to quinoline derivatives having hypoglycemic effect.

Background of the Invention

Heretofore, treatment of diabetes has been performed using a parenteral injection such as an insulin preparation or an oral antidiabetic such as a biguanide compound (e.g., metoformin) or a sulfonylurea compound (e.g., tolbutamide). The insulin preparation has a disadvantageous problem in its troublesome procedure which is inherent to parenteral injection. The orally administrable biguanide compound brings about unfavorable lactic acidosis, and the sulfonylurea compound gives such side-effect as grave hypoglycemia.

Recently, much attention has been paid to 5-substituted benzylthiazoline-2,4-dione derivatives such as troglitazone (European Patent No. 139,421) and pioglitazone hydrochloride (European Patent No. 193,256) which have no noticeable defects such as above and show new pharmacological mechanism such as curing of defective insulin activity (insulin resistance). It has been reported that pioglitazone shows hypoglycemic activity and neutral fat-reducing effect, cures damaged insulin-receptor function, and gives influence to glucose transporter and glycokinase, so that defective insulin activity can be cured.

The present invention has an object to provide a novel quinoline derivative having hypoglycemic effect.

Particularly, the invention has an object to provide a novel quinoline derivative showing hypoglycemic effect by oral administration.

SUMMARY OF THE INVENTION

The present inventors have studied new thiazolidine-2,4-dione derivatives having no benzyl substituent in their 5-positions and, as a result, have discovered that the quinoline derivatives of the following formula (I) have excellent hypoglycemic activity:

$$R^1-(CH_2)_m-Z-(CH_2)_p- \text{[quinoline]} -(CH_2)_q- \overset{O}{\underset{}{\text{C}}}-NH-\overset{}{\underset{E}{\text{C}}}=O \quad (I)$$

in which $R^1$ represents hydrogen, an alkyl group having 1 to 6 carbon atoms, an amino group having the formula of $-NR^4R^5$ in which each of $R^4$ and $R^5$ independently is hydrogen, alkyl of 1 to 6 carbon atoms, phenyl, pyridyl, pyrimidyl or benzoyl, or a phenyl group, a naphthyl group, a cycloalkyl group having 3 to 8 carbon atoms, or a 5 to 8 membered heterocyclic group comprising, as ring-constituting atoms, 1 to 2 nitrogens, oxygens or sulfurs and remaining carbon atoms, each of which may have, as a substituent, alkyl of 1 to 6 carbon atoms, alkoxy of 1 to 6 carbon atoms, halogen, hydroxyl, halogenoalkyl of 1 to 6 carbon atoms, halogenoalkoxy of 1 to 6 carbon atoms, nitro, amino, phenyl, thienyl, furyl, thiazolyl or pyridyl;

Z represents O, S, C=O, or $CH_2$;

E represents S or O;

m is an integer of 0 to 4;

p is an integer of 0 to 4;

q is an integer of 0 to 4; and the double line composed of a broken line and a solid line means a single or double bond.

The present invention has been completed based on the above-mentioned discovery.

In the quinoline derivatives of the invention, particularly preferred are the quinoline derivatives of the following formula (II):

$$R^2-(CH_2)_n-X- \text{[quinoline]} - \overset{O}{\underset{}{\text{C}}}-NH-\overset{}{\underset{S}{\text{C}}}=O \quad (II)$$

in which $R^2$ represents hydrogen, an alkyl group having 1 to 6 carbon atoms, an amino group having the formula of $-NR^6R^7$ in which each of $R^6$ and $R^7$ independently is hydrogen, alkyl of 1 to 6 carbon atoms, phenyl, pyridyl, pyrimidyl or benzoyl, or a phenyl group, a naphthyl group, a cycloalkyl group having 3 to 8 carbon atoms, or a 5 to 8 membered heterocyclic group comprising, as ring-constituting atoms, 1 to 2 nitrogens, oxygens or sulfurs and remaining carbon atoms, each of which may have, as a substituent, alkyl of 1 to 6 carbon atoms, alkoxy of 1 to 6 carbon atoms, halogen, hydroxyl, halogenoalkyl of 1 to 6 carbon atoms, halogenoalkoxy of 1 to 6 carbon atoms, nitro, amino, phenyl, thienyl, furyl, thiazolyl or pyridyl;

X represents O, S, C=O, or $CH_2$;

n is an integer of 0 to 4; and the double line composed of a broken line and a solid line means a single or double bond.

In the quinoline derivatives of the invention, most preferred are the quinoline derivatives of the following formula (III):

$$R^3-(CH_2)_k-O- \text{[quinoline]} - \overset{O}{\underset{}{\text{C}}}-NH-\overset{}{\underset{S}{\text{C}}}=O \quad (III)$$

in which $R^3$ represents a phenyl group, an oxazolyl group, or a pyridyl group, each of which may have, as a substituent, alkyl of 1 to 6 carbon atoms, alkoxy of 1 to 6 carbon atoms, halogen, hydroxyl, halogenoalkyl of 1 to 6 carbon atoms, halogenoalkoxy of 1 to 6 carbon atoms, nitro, amino, phenyl, thienyl, furyl, thiazolyl or pyridyl; and k is an integer of 0 to 4.

PREFERRED EMBODIMENTS OF THE INVENTION

The preferred groups for each symbol seen in the formulas (I), (II), and (III) are described below.

(1) $R^1$ and $R^2$ hydrogen;

an alkyl group having 1 to 6 carbon atoms (e.g., methyl, ethyl, propyl, or isopropyl);

an amino group having the formula of —NR⁴R⁵ or —NR⁶R⁷ (R⁴, R⁵, R⁶ and R⁷ are the same or different from each other) in which each is hydrogen, alkyl of 1 to 6 carbon atoms (e.g., methyl, ethyl, propyl, or isopropyl), phenyl, pyridyl, pyrimidyl or benzoyl, provided that the alkyl, phenyl, pyridyl, pyrimidyl or benzoyl can have a substituent; or a phenyl group, a naphthyl group, a cycloalkyl group having 3 to 8 carbon atoms (e.g., cyclohexyl or cyclopentyl), or a 5 to 8 membered heterocyclic group comprising, as ring-constituting atoms, 1 to 2 nitrogens, oxygens or sulfurs and remaining carbon atoms (e.g., pyridyl, thiazolyl, oxazolyl, thienyl, furyl, pyrrolyl, morpholinyl, indolyl, imidazolyl, or piperidinyl), provided that the phenyl, naphthyl, cycloalkyl and heterocyclic group may have, as a substituent, one or more of alkyl of 1 to 6 carbon atoms (e.g., methyl, ethyl, propyl or isopropyl), alkoxy of 1 to 6 carbon atoms (e.g., methoxy, ethoxy, propoxy or isopropoxy), halogen (e.g., chlorine, fluorine or bromine), hydroxyl, halogenoalkyl of 1 to 6 carbon atoms (e.g., 2-chloroethyl or trifluoromethyl), halogenoalkoxy of 1 to 6 carbon atoms (e.g., 2-chloroethoxy), nitro, amino (e.g., NH₂, methylamino, ethylamino, dimethylamino, or diethylamino), phenyl, thienyl, furyl, thiazolyl or pyridyl, and further provided that the heterocyclic group may be fused with an aromatic ring such as a benzene ring (e.g., benzoxazolyl, benzimidazolyl, benzothiazolyl, or chromanyl).

(2) R³ a phenyl group, an oxazolyl group, or a pyridyl group, provided that the phenyl, oxazolyl or pyridyl group may have, as a substituent, one or more of an alkyl group having 1 to 6 carbon atoms ( e.g., methyl, ethyl, propyl or isopropyl), alkoxy of 1 to 6 carbon atoms (e.g., methoxy, ethoxy, propoxy or isopropoxy), halogen (e.g., chlorine, fluorine or bromine), hydroxyl, halogenoalkyl of 1 to 6 carbon atoms (e.g., 2-chloroethyl or trifluoromethyl), halogenoalkoxy of 1 to 6 carbon atoms (e.g., 2-chloroethoxy), nitro, amino (e.g., NH₂, methylamino, ethylamino, dimethylamino, or diethylamino), phenyl, thienyl, furyl, thiazolyl or pyridyl.

(3) Z and X

O (oxygen), S (sulfur), C=O (carbonyl), or CH₂ (methylene), and O is preferred.

(4) E

S (sulfur) or O (oxygen), and S is preferred.

(5) m, n, p, q, k an integer of 0 to 4, namely, one of 0, 1, 2, 3 and 4; preferred for p and q is 0; and each of m, n and k preferably 1 or 2.

The quinoline ring of the formulas (I) and (II) may have a substituent such as alkyl of 1 to 6 carbon atoms such as methyl, ethyl or propyl, alkoxy of 1 to 6 carbon atoms such as methoxy or ethoxy, or halogen such as chlorine or fluorine.

In the formulas (I) and (II), the group attached to the pyridine ring moiety of quinoline ring, such as thiazolidine-2,4-dion-5-ylmethyl, and the group attached to the benzene ring moiety of the quinoline ring, such as R¹—(CH₂)ₘ—Z—(CH₂)ₚ— is preferably attached to the 3- or 7-position of the quinoline ring, as seen in the formula (III).

The quinoline derivative of the invention may form a pharmacologically acceptable salt. Examples of the salts include an acid salt, namely, a salt of an organic or inorganic acid such as hydrochloric acid or acetic acid, and a basic salt, namely, a salt of an base such as an alkali metal (e.g., sodium or potassium).

Since the carbon atom in the 5-position of the thiazolidine-2,4-dione ring is an asymmetric carbon, the quinoline derivatives of the invention can be any optical isomers and racemates.

The process for preparing the quinoline derivative of the invention can be hereinbelow described with reference to the quinoline derivative of the formula (III), which is a representative quinoline derivative of the invention.

The quinoline derivative of the formula (III) according to the present invention can be prepared, for example, by the below-illustrated preparation process (Synthetic Process-1).

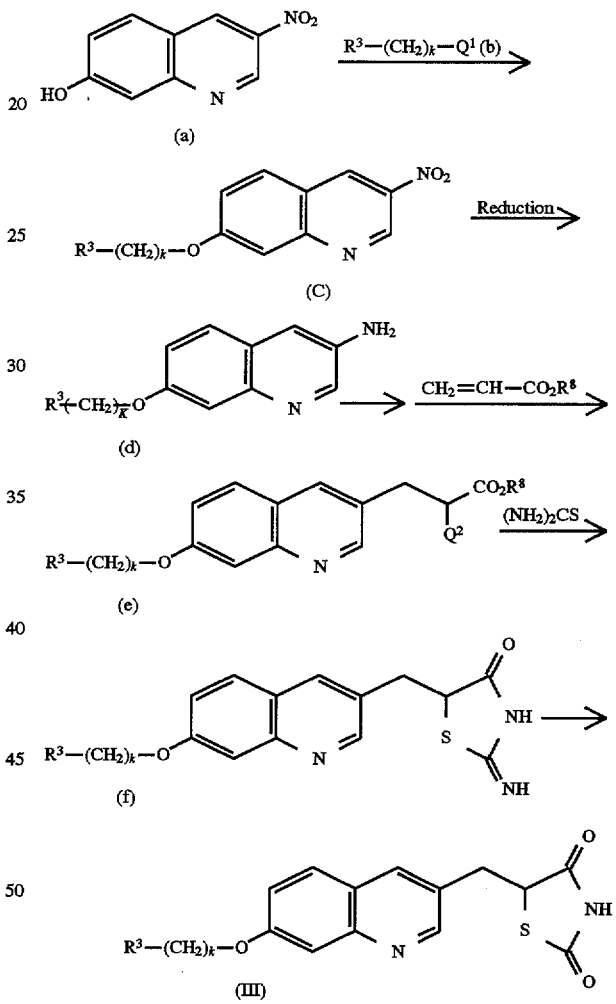

In the above-illustrated reaction scheme, each of Q¹ and Q² represents a halogen atom such as chlorine or bromine, R⁸ represents a lower alkyl group such as methyl or ethyl, and R³ and k have the aforementioned meanings.

The above-illustrated Synthetic Process-1 is further described below.

The 3-nitro-7-hydroxyquinoline of the formula (a) is reacted with a halogenated compound of the formula (b) in an inert solvent such as dimethylformamide (DMF), benzene, toluene, dichloromethane, pyridine, tetrahydrofuran (THF), or dimethylsulfoxide (DMSO) in the presence of a base such as sodium hydride, sodium alkoxide, triethylamine, sodium hydroxide, or sodium carbonate, to give the 3-nitroquinoline derivative of the formula (c).

The 3-nitroquinoline derivative of the formula (c) is then catalytically reduced in an inert solvent such as ethanol, ethyl acetate, methanol or THF, using platinum oxide or palladium/carbon, or reduced by iron or zinc and acetic acid or tin (II) chloride, to give the 3-aminoquinoline derivative of the formula (d).

Thereafter, the 3-aminoquinoline derivative of the formula (d) is reacted with sodium nitrite in an inert solvent such as acetone or methanol in the presence of a hydrohalogenic acid such as aqueous hydrogen bromide or concentrated hydrochloric acid for diazotization, and further reacted with an alkyl acrylate in the presence of a copper catalyst (cuprous oxide or cuprous chloride), to give the 2-halogeno-3-quinolylpropionic acid ester of the formula (e).

Subsequently, the 2-halogeno-3-quinolylpropionic acid ester of the formula (e) is reacted with thiourea in an inert solvent such as ethanol, 2-methoxyethanol, methanol, propanol, or isopropanol, in the presence of sodium acetate, to give the 2-iminothiazolidin-4-one derivative of the formula (f).

Finally, the 2-iminothiazolidin-4-one derivative of the formula (f) is heated under reflux in a mixture of an inorganic acid and alcohol (examples of inorganic acid are hydrochloric acid, sulfuric acid and aqueous hydrogen bromide, and examples of alcohol are ethanol, methanol, propanol and isopropanol), to give the quinoline derivative of the formula (III).

Otherwise, the quinoline derivative of the formula (III) can be prepared by the following process (Synthetic Process-2):

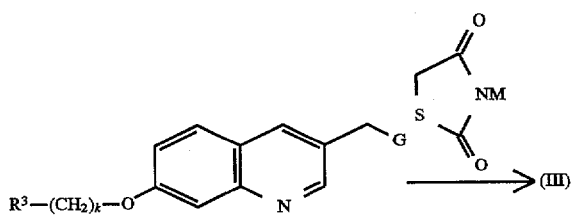

(in the formulas, G represents a releasable group such as chlorine, bromine, iodine, mesyloxy or tosyloxy; M represents an alkali metal such as lithium, sodium or potassium; and $R^3$ and n have the aforementioned meanings).

Thus, the quinoline compound having a releasable group in the 3-position and the alkali metal salt of thiazolidine-2,4-dione are subjected to replacement reaction according to the above-mentioned Synthetic Process-2, to give the quinoline derivative of the formula (III).

The quinoline derivative of the formula (III) can be prepared according to the following preparing process (Synthetic Process-3):

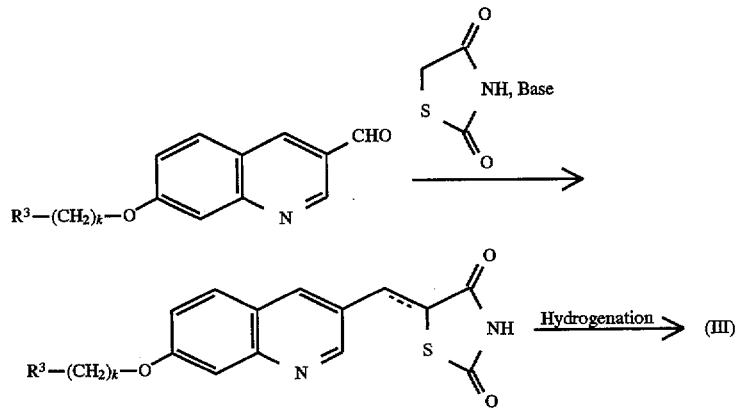

(wherein, $R^3$ and k have the aforementioned meanings.)

Thus, the 3-formylquinoline derivative and thiazolidine-2,4-dione are condensed with dehydration in the presence of a base such as piperidine, piperazine, triethylamine, or sodium carbonate, to give the quinoline derivative of the formula (II), that is, of thiazolidine-5-ylidene type, which is in turn hydrogenated to give the quinoline derivative of the formula (III).

The quinoline derivative of the formula (III) also can be obtained by the following preparing process (Synthetic Process-4):

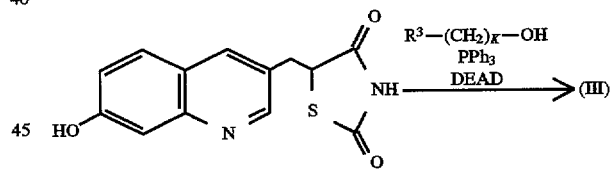

(wherein, $R^2$ and n have the aforementioned meanings.)

Thus, the 7-hydroxyquinoline derivative and an alcohol of $R^3-(CH_2)_k-OH$ such as benzyl alcohol is treated with triphenylphosphine ($PPh_3$) and diethyl azodicarboxylate (DEAD) in THF (solvent), that is, Mitsunobu Reaction, to give the quinoline derivative of the formula (III).

Other compounds represented by the formulas (I) and (II) other than the compounds of the formula (III) can be prepared by processes similar to the above-mentioned synthetic processes.

Representative examples of the quinoline derivatives of the invention are described below:

(1) 5-[(7-benzyloxy-3-quinolyl)methyl]thiazolidine-2,4-dione
(2) 5-[[7-(2-methylbenzyloxy)-3-quinolyl]methyl]-thiazolidine-2,4-dione
(3) 5-[[7-(2-trifluoromethylbenzyloxy)-3-quinolyl]-methyl]thiazolidine-2,4-dione
(4) 5-[[7-(2,5-dimethyl-4-oxazolylmethoxy)-3-quinolyl]methyl]thiazolidine-2,4-dione (5) 5-[[7-(5-methyl-2-phenyl-4-oxazolylmethoxy)-3-quinolyl]methyl]thiazolidine-2,4-dione
(6) 5-[[7-(2-chlorobenzyloxy)-3-quinolyl]methyl]-thiazolidine-2,4-dione
(7) 5-[[7-(2-methoxybenzyloxy)-3-quinolyl]methyl]-thiazolidine-2,4-dione
(8) 5-[[7-(2-dimethylaminobenzyloxy)-3-quinolyl-methyl]thiazolidine-2,4-dione
(9) 5-[[7-(2-nitrobenzyloxy)-3-quinolyl]methyl]-thiazolidine-2,4-dione
(10) 5-[[7-[2-(2-trifluoromethylphenyl)ethoxy]-3-quinolyl]methyl]thiazolidine-2,4-dione
(11) 5-[[7-(5-ethyl-2-pyridylmethoxy)-3-quinolyl]-methyl]thiazolidine-2,4-dione
(12) 5-[[7-(3-pyridylmethoxy)-3-quinolyl]methyl]-thiazolidine-2,4-dione
(13) 5-[[7-(4-pyridylmethoxy)-3-quinolyl]methyl]-thiazolidine-2,4-dione
(14) 5-[[7-(2-phenyl-5-methyl-4-thiazolylmethoxy)-3-quinolyl]methyl]thiazolidine-2,4-dione
(15) 5-[[7-(5-ethyl-2-phenyl-4-thiazolylmethoxy)-3-quinolyl]methyl]thiazolidine-2,4-dione
(16) 5-[[7-[2-(2-thienyl)-5-methyl-4-oxazolylmethoxy]-3-quinolyl]methyl]thiazolidine-2,4-dione
(17) 5-[[7-[2-(2-phenyl-5-methyl-4-oxazolyl)-ethoxy]-3-quinolyl]methyl]thiazolidine-2,4-dione
(18) 5-[[7-(2-furylmethoxy)-3-quinolyl]methyl]-thiazolidine-2,4-dione
(19) 5-[[7-(2-thienylmethoxy)-3-quinolyl]methyl]-thiazolidine-2,4-dione
(20) 5-[[7-(2-quinolylmethoxy)-3-quinolyl]methyl]-thiazolidine-2,4-dione
(21) 5-[[7-(2-piperidinoethoxy)-3-quinolyl]methyl]-thiazolidine-2,4-dione
(22) 5-[[7-[2-(2-benzothiazolyl)ethoxy]-3-quinolyl]-methyl]thiazolidine-2,4-dione
(23) 5-[[7-[2-(2-benzoxazolyl)ethoxy]-3-quinolyl]-methyl]thiazolidine-2,4-dione
(24) 5-[[7-(2-phenyl-4-methyl-5-oxazolylmethoxy)-3-quinolyl]methyl]thiazolidine-2,4-dione
(25) 5-[[7-(2-phenyl-4-methyl-5-thiazolylmethoxy)-3-quinolyl]methyl]thiazolidine-2,4-dione
(26) 5-[[7-(2-morpholinoethoxy)-3-quinolyl]methyl]-thiazolidine-2,4-dione
(27) 5-[[7-(2-trifluoromethylphenylacetyl)-3-quinolyl]methyl]-thiazolidine-2,4-dione
(28) 5-[[7-[2-(2-trifluoromethylphenyl)ethyl]-3-quinolyl]methyl]thiazolidine-2,4-dione
(29) 5-[[7-[2-(2-phenyl-5-methyl-4-oxazolyl)ethyl]-3-quinolyl]methyl]thiazolidine-2,4-dione
(30) 5-[[7-(methylphenylamino)methyl-3-quinolyl]-methylene]thiazolidine-2,4-dione
(31) 5-[[7-(methylphenylamino)methyl-3-quinolyl]-methyl]thiazolidine-2,4-dione
(32) 5-[[7-(2-pyridylmethoxy)-3-quinolyl]methyl]-thiazolidine-2,4-dione
(33) 5-[[7-(2-phenylethyl)-3-quinolyl]methyl]-thiazolidine-2,4-dione
(34) 5-[[7-(3,4-dichlorobenzyloxy)-3-quinolyl]methyl] thiazolidine-2,4-dione
(35) 5-[[7-(4-phenylbenzyloxy)-3-quinolyl]methyl]-thiazolidine-2,4-dione
(36) 5-[[7-(2-naphthylmethoxy)-3-quinolyl]methyl]-thiazolidine-2,4-dione
(37) 5-[[7-(4-trifluoromethylbenzyloxy)-3-quinolyl]-methyl]thiazolidine-2,4-dione
(38) 5-[[7-(2-methylpropyloxy)-3-quinolyl]methyl]-thiazolidine-2,4-dione
(39) 5-[[7-methoxy-3-quinolyl]methyl]thiazolidine-2,4-dione
(40) 5-[[7-(4-ethyl-2-phenyl-5-oxazolylmethoxy)-3-quinolyl]methyl]thiazolidine-2,4-dione
(41) 5-[[7-(1-naphthylmethoxy)-3-quinolyl]methyl]-thiazolidine-2,4-dione
(42) 5-[[7-(4-methoxybenzyloxy)-3-quinolyl]methyl]-thiazolidine-2,4-dione
(43) 5-[[7-hydroxy-3-quinolyl]methyl]thiazolidine-2,4-dione
(44) 5-[[7-(methyl-2-pyridylamino)methyl-3-quinolyl] methyl]thiazolidine-2,4-dione
(45) 5-[[7-(methyl-2-pyridylamino)ethoxy-3-quinolyl] methyl]thiazolidine-2,4-dione
(46) 5-[[7-phenylcarbamoyl-3-quinolyl]methyl] thiazolidine-2,4-dione
(47) 5-[[7-benzoylamino-3-quinolyl]methyl]thiazolidine-2,4-dione
(48) 5-[[7-(4-trifluoromethoxybenzyloxy)-3-quinolyl] methyl]thiazolidine-2,4-dione
(49) 5-[[7-(2-phenyl-5-oxazolylmethoxy)-3-quinolyl]-methyl]thiazolidine-2,4-dione
(50) 5-[[7-(2-benzoxazolylmethoxy)-3-quinolyl]methyl] thiazolidine-2,4-dione
(51) 5-[[7-(4-phenyl-5-methyl-2-oxazolylmethoxy)-3quinolyl]methyl]thiazolidine-2,4-dione
(52) 5-[[6-benzyloxy-2-quinolyl]methyl]thiazolidine-2,4-dione
(53) 5-[[6-(4-trifluorobenzyloxy)-2-quinolyl]methyl] thiazolidine-2,4-dione
(54) 5-[[7-(1-imidazolyl)methyl-3-quinolyl]methyl]-thiazolidine-2,4-dione
(55) 5-[[7-(3-pyridyl) methoxy-3-quinolyl]methyl]-thiazolidine-2,4-dione
(56) 5-[[7-(4-phenyl-2-oxazolyl)methoxy-3-quinolyl]-methyl]thiazolidine-2,4-dione
(57) 5-[[7-(4-trifluoromethoxy)benzyloxy-3-quinolyl] methyl]thiazolidine-2,4-dione
(58) 5-[(7-phenoxymethyl-3-quinolyl)methyl] thiazolidine-2,4-dione
(59) 5-[(6-benzyloxy-2-quinolyl)methylene]thiazolidine-2,4-dione
(60) 5-[(6-benzyloxy-2-quinolyl)methyl]thiazolidine-2,4-dione
(61) 5-[(7-benzyloxy-3-quinolyl)methyl]oxazolidine-2,4-dione
(62) 5-[(7-phenylcarbamoyl-3-quinolyl)methyl] thiazolidine-2,4-dione Pharmacological test data on the hypoglycemic effect of the quinoline derivatives of the invention are described below.

Pharmacological Test

The hypoglycemic effect was examined using KKA$^y$ mouse which was known as insulin-independent diabetic animal. A group of KKA$^y$ mice (9 to 11 weeks) were divided into several groups based on plasma glucose concentration.

Each group included mice having an equal plasma glucose concentration. To the mouse was orally administered a compound of the invention (i.e., the quinoline derivative synthesized in the example given hereinbelow) or pioglitazone (comparison example) in the form of suspension in a 1% methylcellulose solution. The administration was performed once a day and for three days. To the control (mouse having been administered no hypoglycemic agent) was orally administered a 1% methylcellulose solution in the same manner.

After 18 hours from the final administration, blood was collected, and the plasma glucose concentration was examined. The examination was performed in an automatic analytical apparatus (Type 705, available from Hitachi Co., Ltd.) by an enzyme method using Autocella GLU (available from Daiichi Chemicals Co., Ltd.).

The plasma glucose concentration was examined for each of the divided mouse groups, and its ratio (%) per the corresponding value obtained in the control was calculated. The results are set forth in Table 1.

TABLE 1

| Compound | Dosage (mg/kg/day) | Plasma glucose concentration (% per control) |
| --- | --- | --- |
| Pioglitazone | 3 | 86 |
| Pioglitazone | 100 | 54 |
| Example 1 | 80 | 58 |
| Example 2 | 1 | 89 |
|  | 30 | 82 |
| Example 3 | 30 | 82 |
| Example 6 | 30 | 59 |
| Example 7 | 30 | 82 |
| Example 8 | 30 | 79 |
| Example 9 | 30 | 79 |
| Example 11 | 30 | 71 |
| Example 12 | 30 | 77 |
| Example 13 | 30 | 56 |
|  | 10 | 66 |
| Example 16 | 10 | 89 |
| Example 23 | 10 | 73 |
| Example 24 | 30 | 78 |
| Example 26 | 30 | 80 |

Toxicity Test—on rat by four week oral administration

The test compound was suspended in an aqueous 1% methylcellulose solution. The suspension was orally administered into rats of Crj:CD (Sprague-Dawley) strain (female, 5 week age, five rats for one group) once a day for 4 weeks. The dosage of the test compound was 200 mg/kg/day or 600 mg/kg/day for the compound of the invention (Example 6) and 200 mg/kg/day for pioglitazone (pioglitazone hydrochloride, comparison compound).

After the final administration, the rat was allowed to fast overnight, and under ethereal anesthesia its blood was collected from inferior vena cava (EDTA-2K was employed as anticoagulant). The collected blood was measured on its number of erythrocyte, amount of hemoglobin, hematocrit value, and number of platelet using an automatic hemocytometer. The results are set forth in Table 2.

TABLE 2

| Control | Compound of Invention | | Pioglitazone |
| --- | --- | --- | --- |
| Dosage (mg/kg/day) | 0 | 200 | 600 | 200 |
| Erythrocyte ($10^4$/mm$^3$) | 761 ± 53 | 743 ± 45 | 728 ± 33 | 688 ± 41* |
| Hemoglobin (g/dL) | 15.8 ± 0.4 | 15.5 ± 0.7 | 15.1 ± 0.8 | 14.6 ± 0.8* |
| Hematocrit (%) | 45.9 ± 2.2 | 45.6 ± 2.5 | 44.5 ± 1.8 | 43.0 ± 2.6 |
| Platelet ($10^4$/mm$^3$) | 122.9 ± 10.7 | 128.2 ± 8.2 | 123.7 ± 12.6 | 103.2 ± 6.6** |

Remarks: Average ± Standard Deviation
*: $P < 0.05$, **: $P < 0.01$ (based on Control)

The results shown in Tables 1 and 2 indicate that the quinoline derivatives of the invention have significant activity for reduction of blood sugar concentration and low toxicity.

The quinoline derivative of the invention can be administered either orally or parenterally. The orally administrable preparations maybe in the form of pellets, capsules, powders, granules, and syrups. For the parenteral administration, application to mucosa using ophthalmic solutions, inhalations, sprays, or suppositories, application to body surface using ointments, intravenous or subcutaneous administration using injections can be utilized. The oral administrable preparations can be prepared using a conventionally employable excipient, disintegrator, binder, lubricants, dye, diluent, or the like. The excipient maybe glucose or lactose. The disintegrator maybe starch or carboxymethylcellulose calcium. The lubricant maybe magnesium stearate or talc. The binder may be hydroxypropylcellulose, gelatin, or polyvinylpyrrolidone. The parenterally administrable injection may be prepared using distilled water for injection, physiological saline, or Ringer's solution.

The dosage of the quinoline derivative of the invention for adult generally is approximately 0.1 to 200 mg/day when it is administered in the form of an injection, and approximately 1 to 2,000 mg/day when it is orally administered. The dosage can be adjusted depending on age, race, and clinical conditions.

In summary, the quinoline derivative of the invention shows excellent activity for reduction of blood sugar concentration and low toxicity, and therefore are of great value as a remedy, especially an oral administrative remedy, for treatment of diabetes.

The present invention is further described by the following examples, but the examples should not be construed to limit the invention.

EXAMPLE 1

5-[[7-(2-Trifluoromethylbenzyloxy)-3-quinolyl]methyl]-thiazolidine-2,4-dione (1) 3-nitro-7-(2-trifluoromethylbenzyloxy)quinoline In dimethylformamide (DMF, 9 mL) was dissolved 3-nitro-7-hydroxyquinoline (800 mg, 4.24 mmol.). To the solution were added subsequently sodium hydride (168 mg, 4.24 mmol.) and 2-trifluoromethylbenzyl chloride (816 mg, 4.24 mmol.) under chilling with ice. The resulting mixture was stirred overnight at room temperature. After the completion of reaction was confirmed, ethyl acetate and aqueous sodium sulfate were added. The ethyl acetate portion was recovered, washed with water, and dried over sodium sulfate. The solvent was distilled off under reduced pressure, and the residue was purified by silica gel column chromatography (hexane/ethyl acetate=4/1) to give 790 mg of the desired compound as a white crystalline product, yield 53%.

$^1$H-NMR (CDCl$_3$) δ: 5.47 (2H, s), 7.46 (1H, dd, J=2, 9 Hz), 7.5–7.8 (5H, m), 7.94 (1H, d), 8.95 (1H, d, J=2 Hz), 9.59 (1H, d, J=2 Hz)

(2) 3-amino-7-(2-trifluoromethylbenzyloxy)quinoline

In ethanol (30 mL) was suspended 3-nitro-7-(2-trifluoromethylbenzyloxy)quinoline (600 mg, 1.72 mmol.), and to the suspension was added platinum oxide (72 mg). Then, catalytic reduction was performed for 3 hours. After the completion of reaction was confirmed, the reaction mixture was filtered over Celite®, and the filtrate was placed under reduced pressure to leave the desired compound as brown oil in the quantitative yield.

$^1$H-NMR (CDCl$_3$) δ: 5.47 (2H, s), 7.2–7.3 (2H, m), 7.39 (1H, d, J=3 Hz), 7.42 (1H, t, J=8 Hz), 7.53 (1H, d, J=9 Hz), 7.57 (1H, t, J=8 Hz), 7.70 (1H, t, J=8 Hz), 7.79 (1H, d, J=8 Hz), 8.46 (1H, d, J=3 Hz)

(3) methyl2-bromo-3-[7-(2-trifluoromethylbenzyloxy)-3-quinolyl]propionate

In a mixture of acetone and methanol (1.76 mL and 4.46 mL) was dissolved 3-amino-7-(2-trifluoromethylbenzyloxy)quinoline (600 mg, 1.9 mmol.), and to the resulting solution was added aqueous 47% hydrogen bromide (1.35 g).

To the mixture was added aqueous sodium nitrite (149 mg (2.16 mmol.)/0.27 mL) under ice-chilling for 5 minutes, and methyl acrylate (1.04 mL, 11.7 mmol.) was added to the resulting mixture after it was stirred for 20 minutes. Cuprous oxide (17.8 mg) was added gradually to the mixture kept at 37° C. The mixture was then stirred for one hour at the same temperature. After the completion of reaction was confirmed, the solvent was distilled off under reduced pressure. To the residue were added ethyl acetate and aqueous concentrated ammonia, so that the aqueous phase was adjusted to pH 7. The organic portion was recovered, washed with water, and dried over sodium sulfate. The solvent was distilled off under reduced pressure to give 720 mg of the desired compound as crude residue. The crude residue was subjected to the next step without further purification.

$^1$H-NMR (CDCl$_3$) δ: 3.40 (1H, dd, J=7, 14 Hz), 3.62 (1H, dd, J=7, 14 Hz), 3.74 (3H, s), 4.47 (1H, t, J=7 Hz), 5.42 (2H, s), 7.3–7.8 (7H, m), 8.23 (1H, d, J=2 Hz), 8.71 (1H, d, J=2 Hz)

(4) 2-imino-5-[[7-(2-trifluoromethylbenzyloxy)-3-quinolyl]methyl]thiazolidin-4-one In ethanol (10 mL) was dissolved the crude residue (720 mg) of methyl 2-bromo-3-[7-(2-trifluoromethylbenzyloxy)-3-quinolyl]propionate. The solution was heated under reflux for 5 hours after addition of thiourea (117 mg, 1.53 mmol.) and sodium acetate (126 mg, 1.53 mmol.).

After the completion of reaction was confirmed, ethanol was distilled off. To the residue were added ethyl acetate and aqueous sodium hydrogen carbonate. The organic portion was recovered, washed with water, and dried over sodium sulfate.

The solvent was distilled off under reduced pressure. The residual crystalline product was washed with a mixture of hexane and ethyl acetate, to give 203 mg of the desired compound as pale brown crystalline powder (yield after two stages: 25%).

$^1$H-NMR (CD$_3$OD) δ: 3.37 (1H, dd, J=4, 14 Hz), 3.55 (1H, dd, J=7, 14 Hz), 4.7–4.8 (1H, m), 5.42 (2H, s), 7.34 (1H, dd, J=2, 8 Hz), 7.42 (1H, d, J=2 Hz), 7.55 (1H, t, J=8 Hz), 7.65 (1H, t, J=8 Hz), 7.8–7.9 (3H, m), 8.14 (1H, d, J=2 Hz), 8.67 (1H, d, J=2 Hz)

(5) 5-[[7-(2-trifluoromethylbenzyloxy)-3-quinolyl]methyl]thiazolidine-2,4-dione

In a mixture of 2N hydrochloric acid (5 mL) and ethanol (3 mL) was dissolved 2-imino-5-[[7-(2-trifluoromethylbenzyloxy)-3-quinolyl]methyl]thiazolidin-4-one (200 mg, 0.47 mmol.). The resulting solution was heated under reflux for 12 hours. After the completion of reaction was confirmed, ethanol was distilled off. To the residue were added ethyl acetate and aqueous sodium hydrogen carbonate so that the aqueous phase was made to pH 7. The organic portion was recovered, washed with water, and dried over sodium sulfate. The solvent was distilled off under reduced pressure. The residue was purified by silica gel column chromatography (hexane/ethyl acetate=1/8), to give 89 mg of the desired compound as pale brown crystalline powder (yield 44%).

mp: 85°–87° C. (decomp.)

$^1$H-NMR (CDCl$_3$) δ: 3.45 (1H, dd, J=4, 14 Hz), 3.59 (1H, dd, J=7, 14 Hz), 4.68 (1H, dd, J=4, 7 Hz), 5.39 (2H, s), 7.29 (1H, dd, J=2, 9 Hz), 7.43 (1H, t, J=8 Hz), 7.57 (1H, d, J=2 Hz), 7.57 (1H, t, J=8 Hz), 7.71 (1H, d, J=9 Hz), 7.7–7.8 (2H, m), 7.98 (1H, d, J=2 Hz), 8.80 (1H, d, J=2 Hz)

IR (KBr) cm$^{-1}$: 1700, 1620, 1500, 1310, 1160, 1120, 1040, 770.

EXAMPLE 2

5-[[7-(5-Methyl-2-phenyl-4-oxazolylmethoxy)3-quinolyl]methyl]thiazolidine-2,4-dione (1) 3-nitro-7-(5-methyl-2-phenyl-4-oxazolylmethoxy)quinoline In DMF (9 mL) was dissolved 3-nitro-7-hydroxyquinoline (800 mg, 4.24 mmol.). Sodium hydride (168 mg, 4.24 mmol.) and 4-chloromethyl-5-methyl-2-phenyloxazole (880 mg, 4.24 mmol.) were added to the resulting solution under chilling with ice. The mixture was stirred overnight at 50°–60° C. After the completion of reaction was confirmed, ethyl acetate and aqueous sodium sulfate were added. The ethyl acetate portion was recovered, washed with water, and dried over sodium sulfate. The solvent was distilled off under reduced pressure. The residue was purified by silica gel column chromatography (hexane/ethyl acetate=4/1), to give 740 mg of the desired compound as a yellow-white crystalline product (yield 48%).

$^1$H-NMR (CDCl$_3$) δ: 2.50 (3H, s), 5.19 (2H, s), 7.4–7.5 (4H, m), 7.69 (1H, s), 7.92 (1H, d, J=9 Hz), 8.0–8.1 (2H, m), 8.95 (1H, d, J=2 Hz), 9.60 (1H, d, J=2 Hz)

(2) 3-amino-7-(5-methyl-2-phenyl-4-oxazolylmethoxy)quinoline

In a mixture of ethanol (20 mL) and ethyl acetate (10 mL) was suspended 3-nitro-7-(5-methyl-2-phenyl-4-oxazolylmethoxy)quinoline (740 mg, 2.1 mmol.), and to the suspension was added 10% palladium/carbon (50 mg). Then, catalytic reduction was performed overnight. After the completion of reaction was confirmed, the reaction mixture was filtered over Celite®, and the filtrate was placed under reduced pressure to remove the solvent. The residue was purified by silica gel column chromatography (hexane/ethyl acetate=1/7 to ethyl acetate), to give 280 mg of the desired compound as brown oil (yield 42%).

$^1$H-NMR (CDCl$_3$) δ: 2.47 (3H, s), 3.78 (2H, br), 5.09 (2H, s), 7.21 (1H, dd, J=2, 9 Hz), 7.25 (1H, d, 2 Hz), 7.4–7.5 (4H, m), 7.51 (1H, d, J=9 Hz), 8.0–8.2 (2H, m), 8.47 (1H, d, J=2 Hz)

(3) methyl 2-bromo-3-[7-(5-methyl-2-phenyl-4-oxazolylmethoxy)-3-quinolyl]propionate In a mixture of acetone/methanol (1.97 mL/0.78 mL) was dissolved 3-amino-7-(5-methyl-2-phenyl-4-oxazolylmethoxy)quinoline (280 mg, 0.84 mmol.), and to the resulting solution was added aqueous 47% hydrogen bromide (597 mg).

To the mixture was added aqueous sodium nitrite (66 mg (0.96 mmol.)/0.12 mL) under ice-chilling for 5 minutes, and methyl acrylate (0.46 mL, 5.17 mmol.) was added to the resulting mixture after it was stirred for 20 minutes. Cuprous oxide (8 mg) was added gradually to the mixture kept at 37° C. The mixture was then stirred for one hour at the same temperature. After the completion of reaction was confirmed, the solvent was distilled off under reduced pressure. To the residue were added ethyl acetate and aqueous concentrated ammonia, so that the aqueous phase was made to pH 7. The organic portion was recovered, washed with water, and dried over sodium sulfate. The solvent was distilled off under reduced pressure to give 300 mg of the desired compound as crude residue. The crude residue was subjected to the next step without further purification.

$^1$H-NMR (CDCl$_3$) δ: 2.48 (3H, s), 3.41 (1H, dd, J=7, 14 Hz), 3.63 (1H, dd, J=7, 14 Hz), 3.87 (3H, s), 4.48 (1H, t, J=7 Hz), 5.13 (2H, s), 7.2–8.0 (8H, m), 8.23 (1H, d, J=2 Hz), 8.72 (1H, d, J=2 Hz)

(4) 5-[[7-(5-methyl-2-phenyl-4-oxazolylmethoxy)-3-quinolyl]methyl]-2-iminothiazolidin-4-one In ethanol (10 mL) was dissolved the crude residue (300 mg) of methyl 2-bromo-3-[7-(5-methyl-2-phenyl-4-oxazolylmethoxy)-3-quinolyl]propionate. The solution was heated under reflux for 5 hours after addition of thiourea (47 mg, 0.62 mmol.) and sodium acetate (51 mg, 0.62 mmol.).

After the completion of reaction was confirmed, ethanol was distilled off. To the residue were added ethyl acetate and aqueous sodium hydrogen carbonate. The organic portion was recovered, washed with water, and dried over sodium sulfate.

The solvent was distilled off under reduced pressure. The residual crystalline product was washed successively with ether and chloroform, to give 105 mg of the desired compound as pale brown crystalline powder (yield after two stages: 28%).

$^1$H-NMR (CD$_3$OD) δ: 2.51 (3H, s), 3.41 (1H, dd, J=7, 14 Hz), 3.55 (1H, dd, J=4, 14 Hz), 4.4–4.5 (1H, m), 5.19 (2H, s), 7.34 (1H, dd, J=2, 9 Hz), 7.3–7.9 (5H, m), 8.0–8.1 (2H, m), 8.2 (1H, d, J=2 Hz), 8.71 (1H, d, J=2 Hz)

(5) 5-[[7-(5-methyl-2-phenyl-4-oxazolylmethoxy)-3-quinolyl]methyl]thiazolidine-2,4-dione In a mixture of 3N hydrochloric acid (4 mL) and ethanol (2 mL) was dissolved 5-[[7-(5-methyl-2-phenyl-4-oxazolylmethoxy)-3-quinolyl]methyl]-2-iminothiazolidin-4-one (100 mg, 0.22 mmol.). The resulting solution was heated under reflux for 12 hours. After the completion of reaction was confirmed, ethanol was distilled off. To the residue were added ethyl acetate and aqueous sodium hydrogen carbonate. The organic portion was recovered, washed with water, and dried over sodium sulfate. The solvent was distilled off under reduced pressure. The residue was purified by silica gel column chromatography (hexane/ethyl acetate=1/3), to give 11 mg of the desired compound as pale brown crystalline powder (yield 11%).

mp: 195°–200° C. (decomp.)

$^1$H-NMR (CDCl$_3$) δ: 2.46 (3H, s), 3.41 (1H, dd, J=4, 14 Hz), 3.63 (1H, dd, J=7, 14 Hz), 4.68 (1H, dd, J=4, 7 Hz), 5.11 (2H, s), 7.29 (1H, dd, J=2, 8 Hz), 7.4–7.5 (3H, m), 7.63 (1H, d, J=2 Hz), 7.69 (1H, d, J=8 Hz), 7.98 (1H, d, J=2 Hz), 8.0–8.1 (2H, m) 8.81 (1H, d, J=2 Hz)

IR (KBr) cm$^{-1}$: 1700, 1610, 1490, 1320, 1260, 1220, 1180, 1130, 980, 700.

EXAMPLE 3

5-[[7-(5-Ethyl-2-pyridylmethoxy)-3-quinolyl]methyl]thiazolidine-2,4-dione (1) 3-nitro-7-(5-ethyl-2-pyridylmethoxy)quinoline In DMF (9 mL) was dissolved 3-nitro-7-hydroxyquinoline (1.0 g, 5.28 mmol.). Sodium hydride (210 mg, 5.28 mmol.) and 5-ethyl-2-(chloromethyl)pyridine (818 mg, 5.28 mmol.) were added to the resulting solution under chilling with ice. The mixture was stirred overnight at room temperature. After the completion of reaction was confirmed, ethyl acetate and aqueous sodium sulfate were added. The ethyl acetate portion was recovered, washed with water, and dried over sodium sulfate. The solvent was distilled off under reduced pressure. The residue was purified by silica gel column chromatography (chloroform to chloroform/methanol=50/1), to give 710 mg of the desired compound as a yellowish white crystalline product (yield 44%).

$^1$H-NMR (CDCl$_3$) δ: 1.28 (3H, t, J=7 Hz), 2.69 (2H, q, J=7 Hz), 5.37 (2H, s), 7.4–7.5 (2H, m), 7.57 (1H, dd, J=2, 9 Hz), 7.62 (1H, d, J=2 Hz), 7.93 (1H, d, J=9 Hz), 8.50 (1H, d, J=2 Hz), 8.94 (1H, d, J=2 Hz), 9.58 (1H, d, J=2 Hz)

(2) 3-amino-7-(5-ethyl-2-pyridylmethoxy)quinoline

In ethanol (20 mL) was suspended 3-nitro-7-(5-ethyl-2-pyridylmethoxy)quinoline (700 mg, 2.26 mmol.), and to the suspension was added platinum oxide (80 mg). Then, catalytic reduction was performed for 3 hours. After the completion of reaction was confirmed, the reaction mixture was filtered over Celite®, and the filtrate was placed under reduced pressure to give the desired compound as residual oil in a quantitative yield.

$^1$H-NMR (CDCl$_3$) δ: 1.26 (3H, t, J=7 Hz), 2.66 (2H, q, J=7 Hz), 3.79 (2H, br-s), 5.28 (2H, s), 7.23 (1H, d, J=2 Hz), 7.25 (1H, d, J=2 Hz), 7.39 (1H, d, J=2 Hz), 7.45 (1H, d, J=8 Hz), 7.51 (1H, d, J=8 Hz), 7.5–7.6 (1H, m), 8.44 (1H, d, J=2 Hz), 8.46 (1H, d, J=2 Hz)

(3) methyl 2-bromo-3-[7-(5-ethyl-2-pyridylmethoxy)-3-quinolyl]propionate

In a mixture of acetone/methanol (5 mL/2 mL) was dissolved 3-amino-7-(5-ethyl-2-pyridylmethoxy)quinoline (680 mg, 2.43 mmol.), and to the resulting solution was added aqueous 47% hydrogen bromide (1.73 g). To the mixture was added aqueous sodium nitrite (189 mg (2.75 mmol.)/0.3 mL) under ice-chilling for 5 minutes, and methyl acrylate (1.33 mL, 14.9 mmol.) was added to the resulting mixture after it was stirred for 20 minutes. Cuprous oxide (23 mg) was added gradually to the mixture kept at 37° C. The mixture was then stirred for one hour at the same temperature. After the completion of reaction was confirmed, the solvent was distilled off under reduced pressure. To the residue were added ethyl acetate and aqueous concentrated ammonia, so that the aqueous phase was made to pH 7. The organic portion was recovered, washed with water, and dried over sodium sulfate. The solvent was distilled off under reduced pressure to give 790 mg of the desired compound as crude residue. The crude residue was subjected to the next step without further purification.

$^1$H-NMR (CDCl$_3$) δ: 1.26 (3H, t, J=7 Hz), 2.67 (2H, q, J=7 Hz), 3.39 (1H, dd, J=7, 14 Hz), 3.61 (1H, dd, J=7, 14 Hz), 3.74 (3H, s), 4.46 (1H, t, J=7 Hz), 5.31 (2H, s), 7.2–8.0 (6H, m), 7.94 (1H, d, J=2 Hz), 8.70 (1H, d, J=2 Hz)

(4) 5-[[7-(5-ethyl-2-pyridylmethoxy)-3-quinolyl]methyl]-2-iminothiazolidin-4-one In ethanol (20 mL) was dissolved the crude residue (790 mg) of methyl 2-bromo-3-[7-(5-ethyl-2-pyridylmethoxy)-3-quinolyl]propionate. The solution was heated under reflux for 15 hours after addition of thiourea (140 mg, 1.84 mmol.) and sodium acetate (150 mg, 1.84 mmol.). After the completion of reaction was confirmed, ethanol was distilled off. To the residue were added ethyl acetate and aqueous sodium hydrogen carbonate. The organic portion was recovered, washed with water, and dried over sodium sulfate.

The solvent was distilled off under reduced pressure. The residual crystalline crude product was recrystallized successively from chloroform, methanol, and hexane, to give 250 mg of the desired compound as a crude product. The crude product was subjected to the next step without further purification.

$^1$H-NMR (DMSO-$d_6$) δ: 1.20 (3H, t, J=7 Hz), 2.64 (2H, q, J=7 Hz), 3.1–3.2 (1H, m), 3.4–3.5 (1H, m), 4.6–4.7 (1H, m), 5.26 (2H, s), 7.32 (1H, d, J=8 Hz), 7.42 (1H, s), 7.48 (1H, s), 7.67 (1H, d, J=8 Hz), 7.82 (1H, d, J=8 Hz), 8.06 (1H, s), 8.46 (1H, s), 8.7–8.9 (2H, m)

(5) 5-[[7-(5-ethyl-2-pyridylmethoxy)-3-quinolyl]methyl] thiazolidine-2,4-dione

In a mixture of 3N hydrochloric acid (10 mL) and ethanol (10 mL) was dissolved the crude product of 5-[[7-(5-ethyl-2-pyridylmethoxy)-3-quinolyl]methyl]-2-iminothiazolidin-4-one (240 mg). The resulting solution was heated under reflux for 13 hours. After the completion of reaction was confirmed, ethanol was distilled off. To the residue were added ethyl acetate and aqueous sodium hydrogen carbonate. The organic portion was recovered, washed with water, and dried over sodium sulfate. The solvent was distilled off under reduced pressure. The residue was purified by silica gel column chromatography (ethyl acetate), to give 40 of the desired compound as pale brown crystalline powder (yield after three steps, 4%).

mp: 167°–169° C. (decomp.)

$^1$H-NMR (CDCl$_3$) δ: 1.26 (3H, t, J=7 Hz), 2.67 (2H, q, J=7 Hz), 3.50 (2H, d, J=6 Hz), 4.65 (1H, t, J=6 Hz), 5.33 (2H, s), 7.32 (1H, d, J=8 Hz), 7.3–7.6 (3H, m), 7.70 (1H, d, J=9 Hz), 7.96 (1H, s), 8.47 (1H, s), 8.76 (1H, s)

IR (KBr) cm$^{-1}$: 2950, 1700, 1620, 1600, 1560, 1500, 1330, 1270, 1220, 1170.

EXAMPLE 4

5-[[7-(Methylphenylamino)methyl-3-quinolyl]methylene]-thiazolidine-2,4-dione (1) methyl 7-(methylphenylamino)methylquinoline-3-carboxylate In a nitrogen atmosphere, N-methylaniline (383 mg, 3.57 mmol.) was dissolved in DMF (5 mL). Under chilling with ice, 60% sodium hydride (157 mg, 3.93 mmol.) was added to the resulting solution and the mixture was stirred at room temperature for 5 minutes. Under chilling with ice, to this was added dropwise methyl 7-bromomethylquinoline-3-carboxylate (1.0 g, 3.57 mmol.) in dry DMF (10 mL). The resulting mixture was stirred overnight at room temperature. The solvent was distilled off under reduced pressure, and the residue was extracted with chloroform after addition of water (20 mL). The organic portion was washed successively with water and a saturated aqueous sodium chloride solution, and dried over anhydrous sodium sulfate. The solvent was distilled off under reduced pressure, and the residue was purified by silica gel column chromatography (hexane/ethyl acetate=2/1), to give the desired compound as yellow crystalline powder (615 mg, yield: 56%).

$^1$H-NMR (CDCl$_3$) δ: 3.10 (3H, s), 4.01 (3H, s), 4.74 (2H, s), 6.73 (1H, t, J=7 Hz), 6.77 (2H, d, J=8 Hz), 7.21 (2H, dd, J=7, 8 Hz), 7.52 (1H, dd, J=2, 8 Hz), 7.88 (1H, d, J=8 Hz), 8.01 (1H, s), 8.81 (1H, d, J=2 Hz), 9.41 (1H, d, J=2 Hz)

(2) 3-hydroxymethyl-7-(methylphenylamino)methylquinoline

In a nitrogen atmosphere, lithium aluminum hydride (33 mg, 0.88 mmol.) was suspended in tetrahydrofuran (THF, 1 mL). Under chilling with ice, to this was dropwise added the above methyl 7-(methylphenylamino)methyl-quinoline-3-carboxylate (171 mg, 0.56 mmol.) in dry THF (1.5 mL). The resulting mixture was stirred under chilling with ice for 3 hours. To this were added ether (5 mL) and saturated aqueous sodium sulfate solution (3 mL), so that excessive lithium aluminum hydride was decomposed. The organic portion was recovered by decantation, and the residue was washed with ether. The ether washings were combined with the above recovered organic portion. The solvent was distilled off under reduced pressure to give the desired compound as a brown amorphous product (128 mg, yield: 82%).

$^1$H-NMR (CDCl$_3$) δ: 3.06 (3H, s), 4.69 (2H, s), 4.85 (2H, s), 6.71 (1H, t, J=7 Hz), 6.77 (2H, d, J=8 Hz), 7.20 (2H, dd, J=7, 8 Hz), 7.43 (1H, d, J=8 Hz), 7.73 (1H, d, J=8 Hz), 7.91 (1H, s), 8.07 (1H, s), 8.80 (1H, s)

(3) 7-(methylphenylamino)methylquinoline-3-carbaldehyde

The above 3-hydroxymethyl-7-(methylphenylamino) methylquinoline (306 mg, 1.10 mmol.) was dissolved in dry chloroform (8 mL). To this was added manganese dioxide (0.95 g), and the mixture was stirred overnight at room temperature. The reaction mixture was filtered over Celite®, and the residue was washed with chloroform. The chloroform washings were combined with the filtrate. The solvent was distilled off under reduced pressure, to leave the desired compound as brown oil (222 mg, yield: 73%).

$^1$H-NMR (CDCl$_3$, 400 MHz) δ: 3.12 (3H, s), 4.76 (2H, s), 6.74 (1H, t, J=7 Hz), 6.78 (2H, d, J=8 Hz), 7.22 (2H, dd, J=7, 8 Hz), 7.57 (1H, dd, J=2, 8 Hz), 7.95 (1H, d, J=8 Hz), 8.05 (1H, s), 8.60 (1H, s), 9.33 (1H, d, J=2 Hz), 10.2 (1H, s)

(4) 5-[[7-(methylphenylamino)methyl-3-quinolyl] methylene]thiazolidine-2,4-dione The above 7-(methylphenylamino)methylquinoline-3-carbaldehyde (222 mg, 0.8 mmol), 2,4-thiazolidinedione (105 mg, 0.8 mmol.), and piperidine (0.065 mL, 0.66 mmol) were suspended in ethanol (8 mL), and the mixture was heated under reflux overnight. The reaction mixture was cooled in an atmospheric condition, and to this was added 1N hydrochloric acid to adjust the solution to pH 1–2. The mixture was extracted with chloroform after addition of water (10 mL), washed with saturated aqueous sodium chloride solution, and dried over anhydrous sodium sulfate. The solvent was distilled off under reduced pressure, and the residue was purified by silica gel column chromatography (chloroform/methanol=20/1), to give the desired compound as yellow crystalline powder (181 mg, yield: 60%).

$^1$H-NMR (DMSO-$d_6$) δ: 3.10 (3H, s), 4.81 (2H, s), 6.62 (1H, t, J=7 Hz), 6.76 (2H, d, J=8 Hz), 7.15 (2H, dd, J=7, 8 Hz), 7.56 (1H, d, J=8 Hz), 7.79 (1H, s), 7.97 (1H, s), 8.09 (1H, d, J=8 Hz), 8.46 (1H, s), 9.05 (1H, s), 12.7 (1H, brs)

EXAMPLE 5

5-[[7-(Methylphenylamino)methyl-3-quinolyl]methyl] thiazolidine-2,4-dione

The above 5-[[7-(methylphenylamino)methyl-3-quinolyl] methylene]thiazolidine-2,4-dione (164 mg, 0.47 mmol.) was dissolved in 1,4-dioxane (5 mL), and hydrogenated at room temperature for 27 hours after addition of platinum oxide (170 mg). The reaction mixture was filtered over Celite® to remove the catalyst. The residue was washed with methanol. The methanol washings and the filtrate were combined. Then, the solvent was distilled off under reduced pressure. The residue was purified by thin layer chromatography (hexane/ethyl acetate=1/1), to give the desired compound as a yellow amorphous product (39.1 mg, yield: 22%).

$^1$H-NMR (DMSO-$d_6$) δ: 3.08 (3H, s), 3.39 (1H, dd, J=7, 14 Hz), 3.54 (1H, dd, J=5, 14 Hz), 4.76 (2H, s), 5.02 (1H, dd, J=5, 7 Hz), 6.61 (1H, t, J=7 Hz), 6.76 (2H, d, J=8 Hz), 7.14 (2H, dd, J=7, 8 Hz), 7.46 (1H, d, J=8 Hz), 7.73 (1H, s), 7.88 (1H, d, J=8 Hz), 8.14 (1H, s), 8.73 (1H, s), 12.0 (1H, brs)

EXAMPLE 6

5-[(7-Benzyloxy-3-quinolyl)methyl]thiazolidine-2,4-dione (1) 7-benzyloxy-3-nitroquinoline In DMF (75 mL) was dissolved 3-nitro-7-hydroxyquinoline (5.0 g, 26.2 mmol.). Under chilling with ice, to the solution was added sodium hydride (1.15 g, 29 mmol.). After 20 minutes, benzyl bromide (3.4 mL, 29 mmol.) was further added for 10 minutes. The mixture was then stirred overnight at room temperature. After the completion of reaction was confirmed, the mixture was poured into a mixture of ice and water. The precipitated crystalline product was collected by filtration, washed with water, and dried, to give the desired compound (7 g) as a white crystalline product (yield 95%).

$^1$H-NMR (CDCl$_3$) δ: 5.28 (2H, s), 7.36–7.50 (6H, m), 7.61 (1H, d, J=2 Hz), 7.92 (1H, d, J=9 Hz), 8.94 (1H, d, J=2 Hz), 9.58 (1H, d, J=2 Hz)

(2) 3-amino-7-benzyloxyquinoline

Under chilling with ice, to the above 3-nitro-7-benzyloxyquinoline (206 g, 0.82 mol) were added successively concentrated hydrochloric acid (735 mL) and ethanol (368 mL). To the mixture was further added stannic chloride 2 hydrates in ethanol (664 g/735 mL) for one hour. The reaction mixture was allowed to reach room temperature, and stirred overnight under the same condition after addition of 368 mL of ethanol. After the completion of reaction was confirmed, the reaction mixture was adjusted to pH 11 by addition of water and 10N sodium hydroxide under chilling with ice. The reaction mixture was allowed to reach room temperature and to this was added 4 L of ethyl acetate. The precipitated insolubles were removed by filtration and the organic portion was recovered. The organic portion was washed with aqueous sodium chloride solution and dried over sodium sulfate. Ethyl acetate was distilled off, to give 170 g of the desired compound as a slightly greenish white crystalline product (yield 92%). $^1$H-NMR (CDCl$_3$) δ: 3.76 (2H, br), 5.17 (2H, s), 7.19–7.52 (9H, m), 8.45 (1H, d, J=2 Hz)

(3) methyl 3-(7-benzyloxy-3-quinolyl)-2-chloropropionate

The above 3-amino-7-benzyloxyquinoline (2.3 g, 9.2 mmol.) was dissolved in a mixture of acetone and water (25 mL and 6 mL). Under chilling with ice, to the solution was added concentrated hydrochloric acid (2.5 mL). The reaction temperature was set to a temperature of lower than 5° C. The reaction mixture was stirred at 5° C. for 20 minutes after addition of aqueous sodium nitrite solution (833 mg (12 mmol.)/1.6 mL) for 5 minutes. After the stirring was complete, methyl acrylate (6 mL, 67.5 mmol.) was added for 5 minutes. Then, cuprous oxide (120 mg) was gradually added, and the reaction temperature was set to 37° C. Under the condition, the reaction mixture was vigorously stirred. After the completion of reaction was confirmed, acetone was distilled off. To the residue were added ethyl acetate and concentrated aqueous ammonia, so that the aqueous portion reached pH 7. The organic portion was recovered, washed with water, and dried over anhydrous sodium sulfate. The dried mixture was filtered, and the filtrate was placed under reduced pressure to distill off ethyl acetate. The residue was purified by column chromatography (hexane/ethyl acetate= 2/1), to give 1.65 g of the desired compound as a pale yellowish white crystalline product (yield 51%).

$^1$H-NMR (CDCl$_3$, 400 MHz) δ: 3.34 (1H, dd, J=8, 14 Hz), 3.52 (1H, dd, J=8, 14 Hz), 3.74 (3H, s), 4.52 (1H, t, J=8 Hz), 5.22 (2H, s), 7.3–7.5 (7H, m), 7.69 (1H, d, J=9 Hz), 7.94 (1H, d, J=2 Hz), 8.70 (1H, d, J=2 Hz)

(4) 2-imino-5-[(7-benzyloxy-3-quinolyl)methyl]thiazoidin-4-one

The above methyl 3-(7-benzyloxy-3-quinolyl)-2-chloropropionate (12 g, 34 mmol.) was dissolved in 2-methoxyethanol (100 mL). The solution was heated under reflux overnight after addition of thiourea (3.1 g, 48 mmol.) and sodium acetate (3.3 g, 48 mmol.). After the completion of reaction was confirmed, the crystalline precipitate was collected by filtration, washed with water and methanol, and dried under reduced pressure, to give the desired compound as white crystalline powder (7.8 g, yield: 64%).

$^1$H-NMR (DMSO-d$_6$) δ: 3.17 (1H, dd, J=8, 14 Hz), 3.48 (1H, dd, J=4, 14 Hz), 4,69 (1H, dd, J=4, 8 Hz), 5.27 (2H, s), 7.2–7.6 (7H, m), 7.82 (1H, d, J=8 Hz), 8.06 (1H, d, J=2 Hz), 8.66 (1H, s), 8.68 (1H, d, J=2 Hz), 8.86 (1H, s)

(5) 5-[(7-benzyloxy-3-quinolyl)methyl]thiazolidine-2,4-dione

The above imino product (7.8 g, 21.5 mmol.) was dissolved in a mixture of 3N hydrochloric acid (78 mL) and ethanol (78 mL). The mixture was heated under reflux for 12 hours. After the completion of reaction was confirmed, the crystalline precipitate was collected by filtration and washed with water. The crystalline product was suspended in a mixture of water (50 mL)/ethanol (50 mL). The suspension was adjusted to pH 9 by addition of saturated aqueous sodium hydrogen carbonate solution and further stirred for additional one hour. The crystalline product was collected by filtration and dried, to give the desired compound as a slightly yellowish white crystalline product (5.8 g, yield: 74%).

mp: 197°–198° C. (decomp.)

$^1$H-NMR (DMSO-d$_6$) δ: 3.25 (1H, dd, J=8, 14 Hz), 3.51 (1H, dd, J=5, 14 Hz), 5.03 (1H, dd, J=5, 8 Hz), 5.30 (2H, s), 7.35–7.53 (7H, m), 7.93 (1H, d, J=9 Hz), 8.26 (1H, d, J=2 Hz), 8.78 (1H, d, J=2 Hz), 12.05 (1H, bs)

IR (KBr) cm$^{-1}$: 1740, 1680, 1600, 1490, 1380, 1320, 1260, 1210, 1170, 1150, 1120, 1020, 720.

EXAMPLE 7

5-[[7-(2-Pyridylmethoxy)-3-quinolyl]methyl]thiazolidine-2,4-dione

In the same manner as in Example 1, the desired compound was obtained.

mp: 194° C. (decomp.)

$^1$H-NMR (DMSO-d$_6$) δ: 3.35–3.4 (1H, m), 3.50–3.54 (1H, dd, J=5, 14 Hz), 5.20 (1H, dd, J=5, 8 Hz), 5.35 (2H, s), 7.35–7.38 (2H, m), 7.44 (1H, d, J=2 Hz), 7.57 (1H, d, J=8 Hz), 8.84 (1H, dd, J=2, 8 Hz), 7.88 (1H, d, J=9 Hz), 8.12 (1H, d, J=2 Hz), 8.61 (1H, bd, J=4 Hz), 8.70 (1H, d, J=2 Hz), 12.03 (1H, bs)

IR (KBr) cm$^{-1}$: 1703, 1624, 1599, 1495, 1277, 1219, 1169, 1120, 1170, 1147, 1011, 901, 858.

EXAMPLE 8

5-[[7-(2-Phenylethyl)-3-quinolyl]methyl]thiazolidine-2,4-dione

In the same manner as in Example 1, the desired compound was obtained.

mp: 75°–80° C. (decomp.)

$^1$H-NMR (DMSO-d$_6$) δ: 2.98–3.13 (4H, m), 3.37 (1H, dd, J=8, 14 Hz), 3.55 (1H, dd, J=5, 14 Hz), 5.04 (1H, dd, J=5, 8 Hz), 7.2–7.3 (5H, m), 7.51 (1H, dd, J=2, 8 Hz), 7.80 (1H, s), 7.84 (1H, d, J=8 Hz), 8.13 (1H, d, J=2 Hz), 8.74 (1H, d, J=2 Hz), 12.03 (1H, bs)

IR (KBr) cm$^{-1}$: 1745, 1699, 1497, 1454, 1330, 1151, 906.

EXAMPLE 9

5-[[7-(3,4-Dichlorobenzyloxy)-3-quinolyl]methyl]thiazolidine-2,4-dione

In the same manner as in Example 1, the desired compound was obtained.

mp: 212°–216° C. (decomp.)

¹H-NMR (DMSO-d₆) δ: 3.37 (1H, dd, J=8, 15 Hz), 3.52 (1H, dd, J=5, 15 Hz), 5.01 (1H, dd, J=5, 8 Hz), 5.30 (2H, s), 7.34 (1H, d, J=9 Hz), 7.45 (1H, d, J=2 Hz), 7.51 (1H, d, J=8 Hz), 7.67 (1H, d, J=8 Hz), 7.79 (1H, s), 7.87 (1H, d, J=9 Hz), 8.12 (1H, s), 8.71 (1H, d, J=2 Hz), 12.00 (1H, bs)

IR (KBr) cm⁻¹: 3433, 2920, 2713, 2600, 2347, 1745, 1701, 1622, 1579, 1497, 1473, 1406, 1369, 1327, 1265, 1217, 1171, 1124, 1030, 974, 904, 881, 814, 771, 714, 665, 663, 617, 600, 476.

EXAMPLE 10

5-[[7-(4-Phenylbenzyloxy)-3-quinolyl]methyl]thiazolidine-2,4-dione

In the same manner as in Example 1, the desired compound was obtained.

mp: 218°–220° C. (decomp.)

¹H-NMR (DMSO-d₆) δ: 3.4–3.8 (2H, m), 5.0–5.2 (1H, dd, J=4, 7 Hz), 5.49 (2H, s), 7.3–7.8 (11H, m), 8.19 (1H, d, J=9 Hz), 8.58 (1H, s), 8.94 (1H, s)

IR (KBr) cm⁻¹: 1740, 1690, 1630, 1610, 1480, 1425, 1375, 1325, 1300, 1270, 1250, 1225, 1170, 1150, 1120, 990, 890, 820, 755, 680, 600.

EXAMPLE 11

5-[[7-(2-Naphthylmethoxy)-3-quinolyl]methyl]thiazolidine-2,4-dione

In the same manner as in Example 1, the desired compound was obtained.

mp: 198°–200° C. (decomp.)

¹H-NMR (DMSO-d₆) δ: 3.4–3.8 (2H, m), 5.05–5.2 (1H, dd, J=4, 7 Hz), 5.52 (2H, s), 7.5–8.3 (10H, m), 8.62 (1H, s), 8.96 (1H, s)

IR (KBr) cm⁻¹: 1740, 1690, 1630, 1600, 1480, 1425, 1380, 1360, 1325, 1300, 1280, 1250, 1220, 1170, 1150, 1130, 990, 890, 860, 810, 760, 720, 670, 595, 465.

EXAMPLE 12

5-[[7-(2-Dimethylaminobenzyloxy)-3-quinolyl]methyl]thiazolidine-2,4-dione

In the same manner as in Example 1, the desired compound was obtained.

¹H-NMR (CDCl₃) δ: 2.73 (6H, s), 3.38 (1H, dd, J=7, 14 Hz), 3.67 (1H, dd, J=7, 14 Hz), 4.68 (1H, t, J=7 Hz), 5.31 (2H, dd, J=12 Hz), 7.0–7.7 (7H, m), 7.97 (1H, s), 8.83 (1H, d, J=2 Hz)

IR (KBr) cm⁻¹: 1701, 1620, 1497, 1327, 1265, 1214, 1170, 1001, 793, 773.

EXAMPLE 13

5-[[7-(4-Trifluoromethylbenzyloxy)-3-quinolyl]methyl]thiazolidine-2,4-dione

In the same manner as in Example 1, the desired compound was obtained.

mp: 203°–207° C. (decomp.)

¹H-NMR (DMSO-d₆) δ: 3.34 (1H, dd, J=8, 15 Hz), 3.52 (1H, dd, J=5, 15 Hz), 5.00 (1H, dd, J=5, 8 Hz), 5.41 (2H, s), 7.35 (1H, dd, J=2, 9 Hz), 7.46 (1H, d, J=2 Hz), 7.7–7.8 (4H, m), 7.87 (1H, d, J=9 Hz), 8.12 (1H, d, J=2 Hz), 8.70 (1H, d, J=2 Hz), 12.00 (1H, bs)

IR (KBr) cm⁻¹: 3433, 3024, 2951, 2717, 1757, 1701, 1620, 1581, 1497, 1425, 1387, 1329, 1267, 1265, 1221, 1163, 1124, 1068, 1039, 1018, 972, 903, 856, 822, 764, 661, 654, 615, 600, 523, 474.

EXAMPLE 14

5-[[7-(2-Methylpropyloxy)-3-quinolyl]methyl]thiazolidine-2,4-dione

In the same manner as in Example 1, the desired compound was obtained.

mp: 151°–155° C. (decomp.)

¹H-NMR (DMSO-d₆) δ: 1.03 (6H, d, J=7 Hz), 2.10 (1H, m), 3.34 (1H, dd, J=8, 14 Hz), 3.52 (1H, dd, J=5, 14 Hz), 3.91 (2H, d, J=6 Hz), 5.01 (1H, dd, J=5, 8 Hz), 7.24 (1H, dd, J=2, 9 Hz), 7.33 (1H, s), 7.83 (1H, d, J=9 Hz), 8.10 (1H, s), 8.69 (1H, d, J=2 Hz), 12.00 (1H, bs)

IR (KBr) cm⁻¹: 2958, 2931, 2873, 1753, 1703, 1622, 1579, 1497, 1470, 1429, 1331, 1265, 1225, 1173, 1122, 1024, 968, 862, 816, 771, 698, 660, 619, 600, 526, 490.

EXAMPLE 15

5-[(7-Methoxy-3-quinolyl)methyl]thiazolidine-2,4-dione

In the same manner as in Example 1, the desired compound was obtained.

mp: 95°–100° C. (decomp.)

¹H-NMR (DMSO-d₆) δ: 2.75–2.80 (1H, m), 3.50 (1H, dd, J=4, 14 Hz), 3.89 (3H, s), 4.85–4.92 (1H, m), 7.24 (1H, dd, J=2, 8 Hz), 7.35 (1H, d, J=2 Hz), 7.83 (1H, d, J=8 Hz), 8.09 (1H, d, J=2 Hz), 8.70 (1H, d, J=2 Hz), 12.00 (1H, bs)

EXAMPLE 16

5-[[7-(2-Chlorobenzyloxy)-3-quinolyl]methyl]thiazolidine-2,4-dione

In the same manner as in Example 1, the desired compound was obtained.

¹H-NMR (CDCl₃) δ: 3.4–3.6 (2H, m), 4.67 (1H, m), 5.30 (2H, s), 7.2–7.6 (6H, m), 7.71 (1H, d, J=9 Hz), 7.98 (1H, s), 8.79 (1H, d, J=2 Hz)

EXAMPLE 17

5-[[7-[2-(5-Methyl-2-phenyl-4-oxazolyl)ethoxy]-3quinolyl]methyl]thiazolidine -2,4-dione In the same manner as in Example 1, the desired compound was obtained.

¹H-NMR (DMSO-d₆) 67: 2.39 (3H, s), 3.13 (2H, t, J=7 Hz), 3.2–3.6 (2H, m), 4.39 (2H, t, J=7 Hz), 4.75–4.8 (1H, m), 7.2 (1H, dd, J=2, 8 Hz), 7.39 (1H, d, J=2 Hz), 7.4–7.5 (3H, m), 7.81 (1H, d, J=9 Hz), 7.9–8.0 (2H, m), 8.07 (1H, d, J=2 Hz), 8.68 (1H, d, J=2 Hz)

EXAMPLE 18

5-[[7-(5-Ethyl-2-phenyl-4-oxazolylmethoxy)-3-quinolyl]methyl]thiazolidine-2,4-dione In the same manner as in Example 1, the desired compound was obtained.

¹H-NMR (CDCl₃) δ: 1.26 (3H, t, J=7 Hz), 2.82 (2H, q, J=7 Hz), 3.46 (1H, dd, J=4, 14 Hz), 3.59 (1H, m), 4.67 (1H, m), 5.12 (2H, s), 7.2–7.3 (1H, m), 7.43 (3H, m), 7.6–7.7 (2H, m), 7.97–8.04 (3H, m), 8.80 (1H, d, J=2 Hz)

EXAMPLE 19

5-[[7-(5-Methyl-2-phenyl-4-thiazolylmethoxy)-3-quinolyl]methyl]thiazolidine-2,4-dione In the same manner as in Example 1, the desired compound was obtained.

¹H-NMR (CDCl$_3$) δ: 3.47 (3H, s), 3.54 (1H, m), 3.59 (1H, dd, J=4, 14 Hz), 4.68 (1H, m), 5.28 (2H, s), 7.2–7.4 (4H, m), 7.6–7.7 (2H, m), 7.8–8.0 (3H, m), 8.06 (1H, s), 8.80 (1H, d, J=2 Hz)

EXAMPLE 20

5-[[7-(1-Naphthylmethoxy)-3-quinolyl]methyl] thiazolidine-2,4-dione

In the same manner as in Example 1, the desired compound was obtained.

mp: 164°–165° C. (decomp.)

¹H-NMR (DMSO-d$_6$) δ: 3.4–3.6 (2H, m), 5.02 (1H, dd, J=5, 8 Hz), 5.73 (2H, s), 7.32 (1H, dd, J=2, 9 Hz), 7.5–7.75 (6H, m), 7.87 (1H, d, J=9 Hz), 7.95–8.00 (2H, m), 8.13 (1H, d, J=2 Hz), 8.14–8.16 (1H, m), 8.72 (1H, d, J=2 Hz), 12.00 (1H, bs)

IR (KBr) cm$^{-1}$: 1701, 1620, 1497, 1327, 1265, 1214, 1170, 1001, 793, 773.

EXAMPLE 21

5-[[7-(4-Methoxybenzyloxy)-3-quinolyl]methyl] thiazolidine-2,4-dione

In the same manner as in Example 1, the desired compound was obtained.

¹H-NMR (DMSO-d$_6$) δ: 3.34 (1H, dd, J=8, 15 Hz), 3.52 (1H, dd, J=5, 15 Hz), 3.76 (3H, s), 5.00 (1H, dd, J=5, 8 Hz), 5.18 (2H, s), 6.96 (1H, dd, J=2, 9 Hz), 7.28 (1H, dd, J=2 Hz), 7.43 (1H, d, J=8 Hz), 7.83 (1H, d, J=9 Hz), 8.10 (1H, d, J=2 Hz), 8.69 (1H, d, J=2 Hz), 12.00 (1H, bs)

IR (KBr) cm$^{-1}$: 3421, 2926, 2787, 1741, 1736, 1699, 1622, 1585, 1516, 1497, 1421, 1389, 1281, 1248, 1221, 1173, 1126, 1032, 841, 820, 694, 652.

EXAMPLE 22

5-[(7-Hydroxy-3-quinolyl)methyl]thiazolidine-2,4-dione

In the same manner as in Example 1, the desired compound was obtained.

¹H-NMR (DMSO-d$_6$) δ: 3.30 (1H, dd, J=8, 15 Hz), 3.49 (1H, dd, J=5, 15 Hz), 5.00 (1H, dd, J=5, 8 Hz), 7.15 (1H, dd, J=2, 9 Hz), 7.21 (1H, d, J=8 Hz), 7.75 (1H, d, J=9 Hz), 8.03 (1H, d, J=2 Hz), 8.62 (1H, d, J=2 Hz), 10.1 (1H, s), 12.00 (1H, bs)

IR (KBr) cm$^{-1}$: 3159, 3061, 2796, 2561, 1751, 1745, 1703, 1624, 1587, 1477, 1406, 1325, 1279, 1273, 1232, 1230, 1159, 1128, 1024, 962, 933, 906, 858, 839, 814, 768, 742, 692, 677, 471.

EXAMPLE 23

5-[[7-(4-Trifluoromethoxy)benzyloxy-3-quinolyl]methyl] thiazolidine-2,4-dione

In the same manner as in Example 1, the desired compound was obtained.

mp: 210°–125° C. (decomp.)

¹H-NMR (DMSO-d$_6$) δ: 3.54 (2H, m), 5.05 (1H, dd, J=5, 14 Hz), 5.37 (2H, s), 7.42 (2H, d, J=9 Hz), 7.51 (1H, dd, J=2, 9 Hz), 7.62 (1H, d, J=2 Hz), 7.67 (1H, d, J=9 Hz), 8.09 (1H, d, J=9 Hz), 8.60 (1H, d, J=2 Hz), 8.96 (1H, d, J=2 Hz), 12.1 (1H, bs)

IR (KBr) cm$^{-1}$: 2900, 2750, 1740, 1700, 1640, 1600, 1500, 1480, 1420, 1380, 1270, 1220, 1160, 1040, 1020, 850, 820, 690, 670, 650.

EXAMPLE 24

5-[(7-Phenoxymethyl-3-quinolyl)methyl]thiazolidine-2,4-dione

In the same manner as in Example 1, the desired compound was obtained.

¹H-NMR (DMSO-d$_6$) δ: 3.16–3.55 (2H, m), 4.64 (1H, dd, J=4, 8 Hz), 5.33 (2H, s), 6.92–7.32 (5H, m), 7.64 (1H, dd, J=1, 8 Hz), 7.94 (1H, d, J=8 Hz), 8.03 (1H, bs), 8.15 (1H, d, J=2 Hz), 8.77 (1H, d, J=2 Hz)

IR (KBr) cm$^{-1}$: 3427, 3059, 2920, 2728, 1699, 1666, 1567, 1497, 1458, 1379, 1330, 1270, 1234, 1171, 1032, 908, 840, 754, 690.

EXAMPLE 25

5-[(6-Benzyloxy-2-quinolyl)methylene]thiazolidine-2,4dione

In the same manner as in Example 4, the desired compound was obtained.

mp: higher than 250° C.

¹H-NMR (DMSO-d$_6$, 400 MHz) δ: 5.27 (2H, s), 7.34–7.56 (7H, m), 7.87 (1H, d, J=8 Hz), 7.92 (1H, s), 8.03 (1H, d, J=9 Hz), 8.33 (1H, d, J=8 Hz), 12.4 (1H, s)

IR (KBr) cm$^{-1}$: 3128, 3026, 1738, 1678, 1612, 1429, 1385, 1340, 1302, 1230, 1170, 1116, 860, 835, 742, 701, 636, 611.

EXAMPLE 26

5-[(6-Benzyloxy-2-quinolyl)methyl]thiazolidine-2,4-dione

In the same manner as in Example 5, the desired compound was obtained.

mp: 144°–146° C.

¹H-NMR (DMSO-d$_6$, 400 MHz) δ: 3.37 (1H, dd, J=10, 17 Hz), 3.83 (1H, dd, J=3, 17 Hz), 5.03 (1H, dd, J=3, 10 Hz), 5.26 (2H, s), 7.38–7.55 (8H, m), 7.84 (1H, m), 8.21 (1H, d), 12.3 (1H, s)

IR (KBr) cm$^{-1}$: 3182, 3056, 3029, 1743, 1681, 1621, 1600, 1500, 1383, 1338, 1321, 1301, 1234, 1171, 1155, 1113, 1012, 858, 827, 741, 694, 530.

EXAMPLE 27

5-[(7-Benzyloxy-3-quinolyl)methyl]oxazolidine-2,4-dione (1) ethyl 2-hydroxy-3-(7-benzyloxy-3-quinolyl)propionate In water (7 mL) were suspended 2-chloro-3-(7-benzyloxy-3-quinolyl)propionic acid (1.02 g, 2.99 mmol.), calcium carbonate (280 mg, 2.80 mmol.), and sodium hydroxide (120 mg, 3.00 mmol.), and the resulting mixture was heated under reflux for 24 hours. The reaction mixture was cooled, and extracted with ethyl acetate (20 mL×4) after it was made acidic by addition of 6N hydrochloric acid. The organic portion was washed with water, and dried over anhydrous magnesium sulfate. The solvent was then distilled off under reduced pressure. The resulting residue was heated under reflux for 3 hours after addition of ethanol (10 mL) and sulfuric acid (0.050 mL). The reaction mixture was extracted with ethyl acetate (20 mL×4) after addition of water (50 mL). The organic portion was washed with water, and dried over anhydrous sodium sulfate. Then, the solvent was distilled off under reduced pressure. The residue was purified by silica gel column chromatography (hexane/ethyl acetate=1/2), to give 162 mg of the desired compound as a yellow crystalline product (yield 15%).

¹H-NMR (DMSO-d$_6$, 400 MHz) δ: 1.28 (3H, t, J=7 Hz), 3.10 (1H, dd, J=7, 14 Hz), 3.25 (1H, dd, J=4, 14 Hz), 4.23

(2H, dd, J=1, 7 Hz), 4.50 (1H, dd, J=4, 7 Hz), 5.17 (2H, s), 7.23 (1H, dd, J=2, 9 Hz), 7.34 (1H, d, J=7 Hz), 7.40 (2H, t, J=7 Hz), 7.44 (1H, d, J=2 Hz), 7.48 (2H, t, J=7 Hz), 7.60 (1H, d, J=9 Hz), 7.92 (1H, s), 8.66 (1H, d, J=2 Hz)

(2) 5-[(7-benzyloxy-3-quinolyl)methyl]oxazolidine-2,4dione

In ethanol (1.5 mL) were suspended ethyl 2-hydroxy-3-(7-benzyloxy-3-quinolyl)propionate (162 mg, 0.461 mmol.), urea (48.7 mg, 0.804 mmol.) and sodium methoxide (28% methanolic solution, 0.12 mL, 0.622 mmol.). The resulting suspension was stirred for one hour at room temperature, and then heated under reflux for 4 hours. The reaction mixture was cooled, and neutralized by addition of saturated aqueous sodium hydrogen carbonate solution after addition of 1N hydrochloric acid (1.0 mL) and water (2.0 mL). Insolubles were collected, washed with ethyl acetate and ether, and dried under reduced pressure, to give 110 mg of the desired compound as white crystalline powder (yield 66%).

mp: 178°–190° C. (decomp.)

$^1$H-NMR (DMSO-$d_6$) δ:
2.97 (1H, dd, J=8, 14 Hz), 3.13 (1H, dd, J=4, 14 Hz), 4.25 (1H, dd, J=4, 8 Hz), 5.27 (2H, s), 7.30 (1H, dd, J=2, 9 Hz), 7.35 (1H, d, J=7 Hz), 7.41 (2H, t, J=7 Hz), 7.45 (1H, d, J=2 Hz), 7.51 (2H, d, J=7 Hz), 7.84 (1H, d, J=9 Hz), 8.10 (1H, s), 8.69 (1H, d, J=2 Hz), 12.5 (1H, brs)

IR (KBr) cm$^{-1}$: 3483, 3433, 3032, 2931, 2881, 1957, 1707, 1701, 1622, 1498, 1491, 1454, 1429, 1385, 1325, 1263, 1261, 1240, 1223, 1192, 1126, 1078, 1016, 999, 916, 841, 820, 787, 741, 669, 661, 606, 528, 467.

EXAMPLE 28

5-[(7-Phenylcarbamoyl-3-quinolyl)methyl]thiazolidine-2,4-dione

In the same manner as in Example 1, the desired compound was obtained.

mp: 165°–170° C. (decomp.)

$^1$H-NMR (CDCl$_3$+CD$_3$OD) δ: 3.75 (2H, m), 4.85 (1H, m), 7.35 (1H, m), 7.84 (1H, d, J=7 Hz), 8.24 (1H, d, J=8 Hz), 8.83 (1H, s), 9.14 (2H, m)

IR (KBr) cm$^{-1}$: 1750, 1700, 1600, 1540, 1490, 1440, 1390, 1320, 760.

What is claimed is:

1. A quinoline compound having the formula (I):

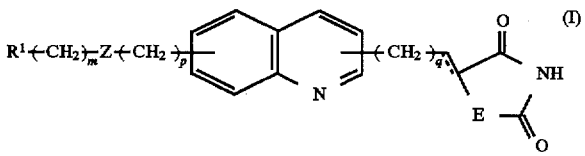

in which $R^1$ represents
hydrogen,
an alkyl group having 1 to 6 carbon atoms, an amino group having the formula of —NR$^4$R$^5$ in which each of R$^4$ and R$^5$ independently is hydrogen, alkyl of 1 to 6 carbon atoms, phenyl, pyridyl, pyrimidyl or benzoyl, or
  a phenyl group, a naphthyl group, a cycloalkyl group having 3 to 8 carbon atoms, or a 5 to 8 membered heterocyclic group comprising, as ring-constituting atoms, 1 to 2 nitrogens, oxygens or sulfurs and remaining carbon atoms, each of which may have, as a substituent, alkyl of 1 to 6 carbon atoms, alkoxy of 1 to 6 carbon atoms, halogen, hydroxyl, halogenoalkyl of 1 to 6 carbon atoms, halogenoalkoxy of 1 to 6 carbon atoms, nitro, amino, phenyl, thienyl, furyl, thiazolyl or pyridyl;

Z represents O, S, C=O, or CH$_2$;

E represents S or O;

m is an integer of 0 to 4;

p is an integer of 0 to 4;

q is an integer of 0 to 4; and the double line composed of a broken line and a solid line means a single or double bond.

2. A quinoline compound having the formula (II):

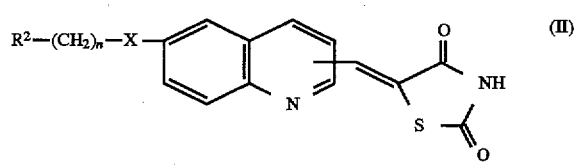

in which $R^2$ represents
hydrogen,
an alkyl group having 1 to 6 carbon atoms, an amino group having the formula of —NR$^6$R$^7$ in which each of R$^6$ and R$^7$ independently is hydrogen, alkyl of 1 to 6 carbon atoms, phenyl, pyridyl, pyrimidyl or benzoyl, or
  a phenyl group, a naphthyl group, a cycloalkyl group having 3 to 8 carbon atoms, or a 5 to 8 membered heterocyclic group comprising, as ring-constituting atoms, 1 to 2 nitrogens, oxygens or sulfurs and remaining carbon atoms, each of which may have, as a substituent, alkyl of 1 to 6 carbon atoms, alkoxy of 1 to 6 carbon atoms, halogen, hydroxyl, halogenoalkyl of 1 to 6 carbon atoms, halogenoalkoxy of 1 to 6 carbon atoms, nitro, amino, phenyl, thienyl, furyl, thiazolyl or pyridyl;

X represents O, S, C=O, or CH$_2$;

n is an integer of 0 to 4; and the double line composed of a broken line and a solid line means a single or double bond.

3. A quinoline compound having the formula (III):

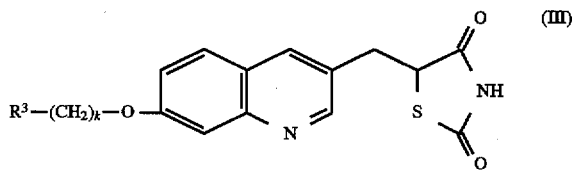

in which $R^3$ represents a phenyl group, an oxazolyl group, or a pyridyl group, each of which may have, as a substituent, alkyl of 1 to 6 carbon atoms, alkoxy of 1 to 6 carbon atoms, halogen, hydroxyl, halogenoalkyl of 1 to 6 carbon atoms, halogenoalkoxy of 1 to 6 carbon atoms, nitro, amino, phenyl, thienyl, furyl, thiazolyl or pyridyl; and k is an integer of 0 to 4.

* * * * *